United States Patent [19]
Marion et al.

[11] Patent Number: 6,143,936
[45] Date of Patent: Nov. 7, 2000

[54] PROCESS FOR PRODUCING AN ETHER AND AN OLEFIN FROM A HYDROCARBON CUT CONTAINING AT LEAST ONE TERTIARY OLEFIN BY SYNTHESIZING THEN DECOMPOSING AN ETHER, COMPRISING A FIRST STEP FOR PURIFYING THE OLEFIN BY WASHING WITH WATER

[75] Inventors: Marie-Claire Marion, Villeurbanne; Vincent Coupard, Lyons; Alain Forestiere, Vernaison; Philippe Travers, Rueil Malmaison; Jean-Charles Viltard, Valence, all of France

[73] Assignee: Institut Francais du Petrole, Rueil-Malmaison Cedex, France

[21] Appl. No.: 09/053,060

[22] Filed: Apr. 1, 1998

[30] Foreign Application Priority Data

Apr. 2, 1997 [FR] France .................................. 97 04116

[51] Int. Cl.[7] .............................. C07C 41/00; C07C 1/00
[52] U.S. Cl. .......................... 568/697; 568/579; 585/324; 585/510; 585/515; 585/638; 585/639; 585/640
[58] Field of Search ..................................... 585/639, 329, 585/638, 640, 510, 515; 568/697, 579

[56] References Cited

U.S. PATENT DOCUMENTS

| | | | |
|---|---|---|---|
| 4,447,668 | 5/1984 | Smith, Jr. et al. | 585/639 |
| 5,354,831 | 10/1994 | Panster et al. . | |
| 5,567,860 | 10/1996 | Mowry et al. | 585/639 |

FOREIGN PATENT DOCUMENTS

| | | |
|---|---|---|
| 0869107 | 10/1998 | European Pat. Off. . |
| 2 527 201 | 11/1983 | France . |
| 257201 | 11/1983 | France . |
| 2669021 | 5/1992 | France . |

*Primary Examiner*—Elli Peselev
*Attorney, Agent, or Firm*—Millen, White, Zelano & Branigan, P.C.

[57] ABSTRACT

A process for producing an ether and an olefin from a hydrocarbon cut containing at least one tertiary olefin, comprises synthesis of at least one tertiary alkyl ether then fractionation to obtain an organic fraction (E1) which is enriched in the tertiary alkyl ether which is decomposed into a product containing at least one alcohol and at least one tertiary olefin, which is purified in a water washing extraction zone (L1) to obtain an aqueous fraction (A1) containing the major portion of the alcohol and a fraction (B1) containing the major portion of the tertiary olefin, at least a portion of fraction (B1) being sent to a separation zone (Co1) from which an aqueous liquid fraction (La1) and a liquid fraction (Lb1) containing the major portion of the tertiary olefin are recovered.

23 Claims, 5 Drawing Sheets

PROCESS FOR PRODUCING AN ETHER AND AN OLEFIN FROM A HYDROCARBON CUT CONTAINING AT LEAST ONE TERTIARY OLEFIN BY SYNTHESIZING THEN DECOMPOSING AN ETHER, COMPRISING A FIRST STEP FOR PURIFYING THE OLEFIN BY WASHING WITH WATER

FIELD OF THE INVENTION

The invention concerns an integrated process for synthesising an ether and a tertiary olefin, generally pure, from hydrocarbon cuts containing at least one tertiary olefin, comprising a step for etherification of the hydrocarbon cut by at least one alcohol, in which a product is formed which contains at least one tertiary alkyl ether which is then sent to a tertiary alkyl ether decomposition zone from which a product comprising at least one tertiary olefin, Generally of high purity, is recovered. In particular, it relates to a process for the production of very high purity isobutene from a $C_4$ hydrocarbon cut containing it, comprising formation, from this cut and methanol, of methyl-tertio-butyl-ether (MTBE), then decomposition of the MTBE and purification and/or fractionation of the decomposition product to methyl alcohol and purified isobutene. The process of the present invention is also applicable to the synthesis of any tertiary olefin from a tertiary alkyl ether [for example ETBE (ethyl-tertio-butyl-ether), ETAE (tertio-amyl-methyl-ether), TAME (tertio-amyl-methyl-ether), and isopropyl-t-rtio-butyl-ether]. The remainder of the description of the present invention, in particular the operating conditions, is given by way of indication for the synthesis of isobutene from hydrocarbon cuts comprising essentially hydrocarbons containing 4 carbon atoms (among them isobutene) by synthesis and decomposition of MTBE.

BACKGROUND OF THE INVENTION

A variety of routes for producing high purity isobutene can be employed industrially. The oldest is the sulphuric acid extraction process, but it is expensive and obsolete; it is known to be a contaminating process as waste acid is discharged. Further, the isobutene yield does not exceed 90%. The company ARCO uses tertio-butyl alcohol (TBA) dehydration, TBA being a by-product from their propylene oxide production process. The isobutane dehydrogenation process was developed during the last few years as a result of the large and increasing demand for MTBE. However, that process can only be profitable with very large production capacities.

High purity isobutene production from cracking MTBE is as suitable for small capacities as for large capacities. Further, such a route benefits from the infrastructure generated by the increasing importance of ethers in reformulated gasoline. A number of refineries throughout the world have MTBE production installations, for example. Further, there is a global exchange market for MTBE. This means that the production of high purity isobutene from MTBE can readily be carried out anywhere in the world, in and remote from refineries.

The concept of producing isobutene by decomposing an ether, more particularly MTBE, has long been known, but prior art processes have suffered from certain disadvantages.

In the process developed by SUMITOMO described, for example, in European patent application EP-A-0 068 785, the MTBE decomposition reaction is carried out in the liquid phase, in the presence of a solid acid catalyst which is an ion exchange resin. Two product streams are obtained: isobutene and methanol. As described, isobutene is obtained directly overhead from a distillation column with no other purification step. The isobutene obtained contains a certain number of impurities, beginning with a small fraction of methanol which is azeotropically distilled from dimethylether (DME), which is a volatile compound formed by condensing methanol in the presence of an acid catalyst. It is probable that the purity of the isobutene is insufficient for use in the production of polyisobutene or other copolymers. Further, there is no apparent way of avoiding the accumulation of heavy impurities such as dimers of isobutene or methyl sec-butyl ether (MSBE), which in the long run results in a fatal reduction of product purity.

In the process developed by ERDOLCHEMIE, described in United States patent U.S. Pat. No. 4,409,421, for example, isobutene is purified by eliminating residual alcohol entrained with the tertiary olefin by adsorption. This method has the disadvantage of requiring regular regeneration of the adsorbent. Further, the problem of recovering the major portion of the alcohol from the decomposition step is not solved.

More recently in U.S. Pat. No. 5,095,164, the same company has described carrying out the decomposition reaction in a distillation apparatus. The catalyst is placed in the bottom of the column at the reboiler level. That particular implementation limits the reaction temperature, which is directly imposed by the nature of the ether and the operating pressure. Further, it apparently encourages the formation of reaction by-products such as the formation of dimers of isobutene and/or dimethylether formation. In this regard, the quality and/or development of the products is not clearly explained.

In U.S. Pat. No. 4,287,379, BASF describes a scheme which integrates both ether synthesis, its separation then the ether decomposition step to produce the isobutene. However, in order to avoid certain purification steps, etherification is carried out with a $C_3$ or $C_4$ alcohol, which is a major disadvantage as regards the international MTBE market.

We can also cite the two flowcharts of the SNAMPROGETTI process presented in "Chemical Economy & Engineering Review", vol. 14, n 6, June 1982, including both an MTBE synthesis step and an MTBE decomposition step for the production of isobutene. Such schemes use a zone for fractionation by distillation immediately after the reactional decomposition zone. Since the treated product is rich in methanol, fractionation results in the production of two effluents each containing the alcohol: in the overhead effluent, the alcohol is entrained azeotropically, and in the bottoms effluent the majority of the alcohol obtained in the ether decomposition step is obtained. In such a scheme, alcohol recovery is thus complicated since it must be recovered both from the overhead effluent from the fractionation column and from the bottoms effluent from that column.

One method of rendering alcohol recovery easier is to carry out an alcohol extraction step immediately after the ether decomposition step. This concept is described to a greater or lesser extent in International patent application WO 91/01804 in the name of EXXON and in Rumanian patent application RO 105 954 in the name of CAROM. However, those proposed processes have a certain number of disadvantages. According to the description in application RO 105 954, the decomposition step takes place in an adiabatic reactor in the presence of steam. The presence of water in the reaction medium is deleterious to the selectivity of the decomposition reaction as isobutene is lost by reaction with water to form tertio-butyl alcohol (TBA). Further, the system also requires the provision of a supplementary decanting step. In addition, the alcohol recovery column (column C2 in the figure in that patent) is enormous due to the quantities of water used.

International patent application WO 91/01804 principally describes the possibility of regenerating the catalyst, which is preferably a clay. Thus the ether and/or alcohol extracted during the washing step is returned to the reaction section to be used as a regeneration stream. Such a batch operation, which alternates the reaction period and regeneration period in a steady frequency, results from using a catalyst which is not stable over time. The single example given concerns the decomposition of tertio-amyl-methyl-ether (TAME) to form isoamylenes, a reaction which is less demanding as regards temperature than MTBE decomposition with respect to the position of the thermodynamic equilibrium. Thus there are difficulties in operation and also difficulties in inserting it into a Generally integrated scheme where neighbouring units operate continuously (for example the etherification unit for synthesis of MTBE or TAME). It is thus necessary to store products upstream and downstream, involving additional costs and constant management.

SUMMARY OF THE INVENTION

The process of the invention can overcome the disadvantages of the systems described in the prior art publications cited above. It concerns a process for the production of tertiary olefin(s) generally of a (very) high purity, from a hydrocarbon cut containing it, by a method comprising forming then decomposing at least one tertiary alkyl ether. The process is thus also a process which is suitable for upgrading tertiary olefins contained in hydrocarbon cuts in the form of purified tertiary olefins, particularly for use in forming polymers and/or copolymers and/or in the form of tertiary alkyl ethers, particularly for use as additives for internal combustion engine fuels.

The invention concerns a process comprising synthesising tertiary alkyl ether(s), in particular MTBE or ETBE (ethyl-tertio-butyl-ether), and decomposing at least a portion of these tertiary alkyl ether(s), in particular MTBE or ETBE, to produce high purity tertiary olefin(s), in particular isobutene. When decomposing other ethers, a mixture can be obtained which contains a plurality of tertiary olefins. Thus in the case of TAME decomposition, a mixture containing 2-methyl-1-butene and 2-methyl-2-butene is obtained.

In addition to the reaction zones themselves, the process of the invention comprises zones for purification, recovery or recycling the various products to optimise upgrading of the products used and to minimise losses.

BRIEF DESCRIPTION OF THE DRAWINGS

FIGS. 1 to 5 are flowcharts each illustrating one of the multiple variations of the process of the present invention. The dotted lines show the various possible options, namely recycling options and optional apparatus in the variation under consideration. The process of the present invention is described with reference to these figures with the aim of facilitating comprehension. In the figures, similar means are designated by the same reference letters and numbers. FIG. 1 illustrates the most general form of the process of the invention and is described below.

The present invention concerns a process tor the production of a pure tertiary olefin and/or a tertiary alkyl ether from a hydrocarbon cut containing at least one etherifiable tertiary olefin, the process comprising:

a) a step for forming at least one tertiary alkyl ether bv bringing at least one hydrocarbon cut containing at least one etherifiable tertiary olefin into contact with at least one alcohol, generally a primary or secondary alcohol, preferably a primary alcohol generally containing 1 to 6, preferably 1 to 4, carbon atoms per molecule, preferably methyl alcohol or ethyl alcohol or isopropanol, more preferably methyl alcohol or ethyl alcohol, in a reaction zone generally comprising at least one reactor (R100) and generally containing an etherification catalyst, under conditions for transforming at least a portion of the tertiary olefin into a tertiary alkyl ether;

b) a step for separating the major portion of the product from step a) into an organic fraction (O1) which is depleted in tertiary alkyl ether, preferably containing practically no tertiary alkyl ether, and an organic fraction (E1), enriched in the tertiary alkyl ether, preferably containing practically all of the tertiary alkyl ether formed during step a);

c) a step for decomposing at least a portion of the tertiary alkyl ether contained in the organic fraction (E1) from step b), in a reaction zone (R1) generally comprising at least one reactor containing a catalyst for decomposing said ether, into a product (P1) containing at least one alcohol and at least one tertiary olefin;

d) a step for purifying at least a portion of product (P1) from step c), preferably all of product (P1), in a water washing extraction zone (L1) from which an aqueous fraction (A1) containing the major portion of the alcohol initially present in said portion of product (P1) and a fraction (B1) containing the major portion of the tertiary olefin initially present in product (P1) are obtained, said fraction (B1) containing said tertiary olefin, water, possibly ether [not decomposed in step c)] and possibly light compounds and generally being depleted in alcohol or containing a very small proportion thereof (for example less than 10%, normally less than 5% and usually less than 2% by weight);

said process being characterized in that it comprises a step e) in which at least a portion of fraction (B1) is sent to a separation zone (Co1), from which a liquid aqueous fraction (La1) and a liquid organic fraction (Lb1) containing the major portion of the tertiary olefin initially present in said portion of the fraction (B1) are recovered, said fraction (Lb1) containing said tertiary olefin, possibly ether, possibly light compounds and possibly heavy compounds.

In a particular implementation of the process of the invention, a portion of the organic fraction (E1) containing the tertiary alkyl ether is sent to the motor fuel pool and the other portion is sent to tertiary alkyl ether decomposition step c).

DETAILED DESCRIPTION OF THE DRAWINGS

Figure 1:
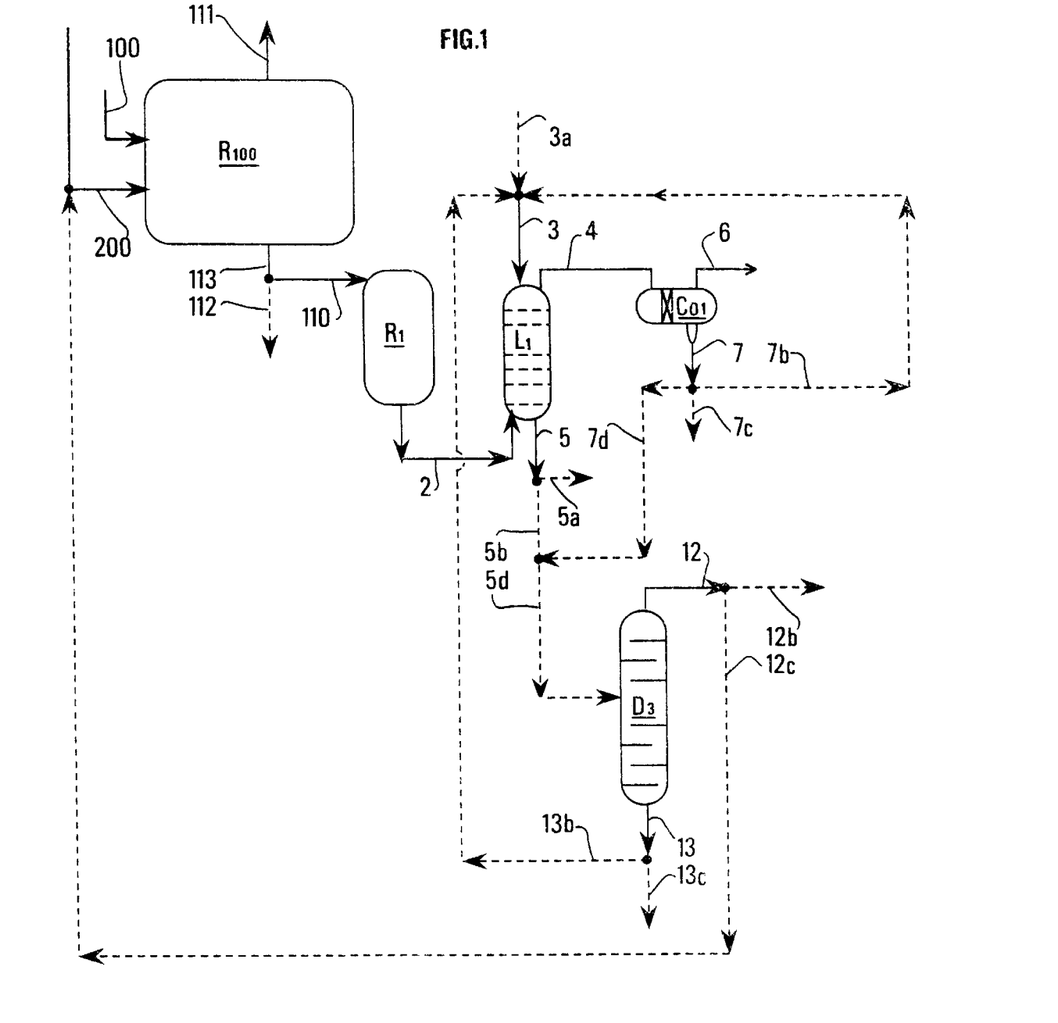
Figure 2:
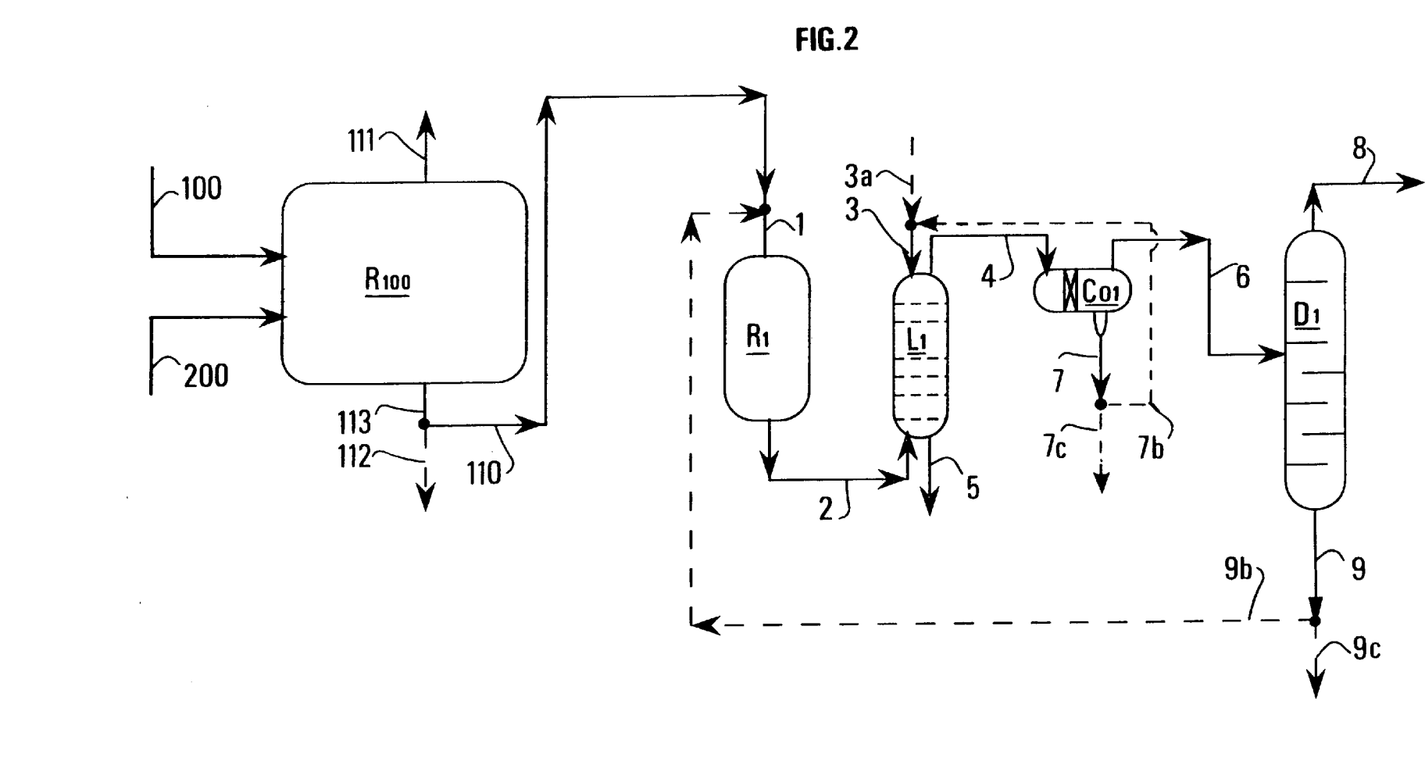
Figure 3:
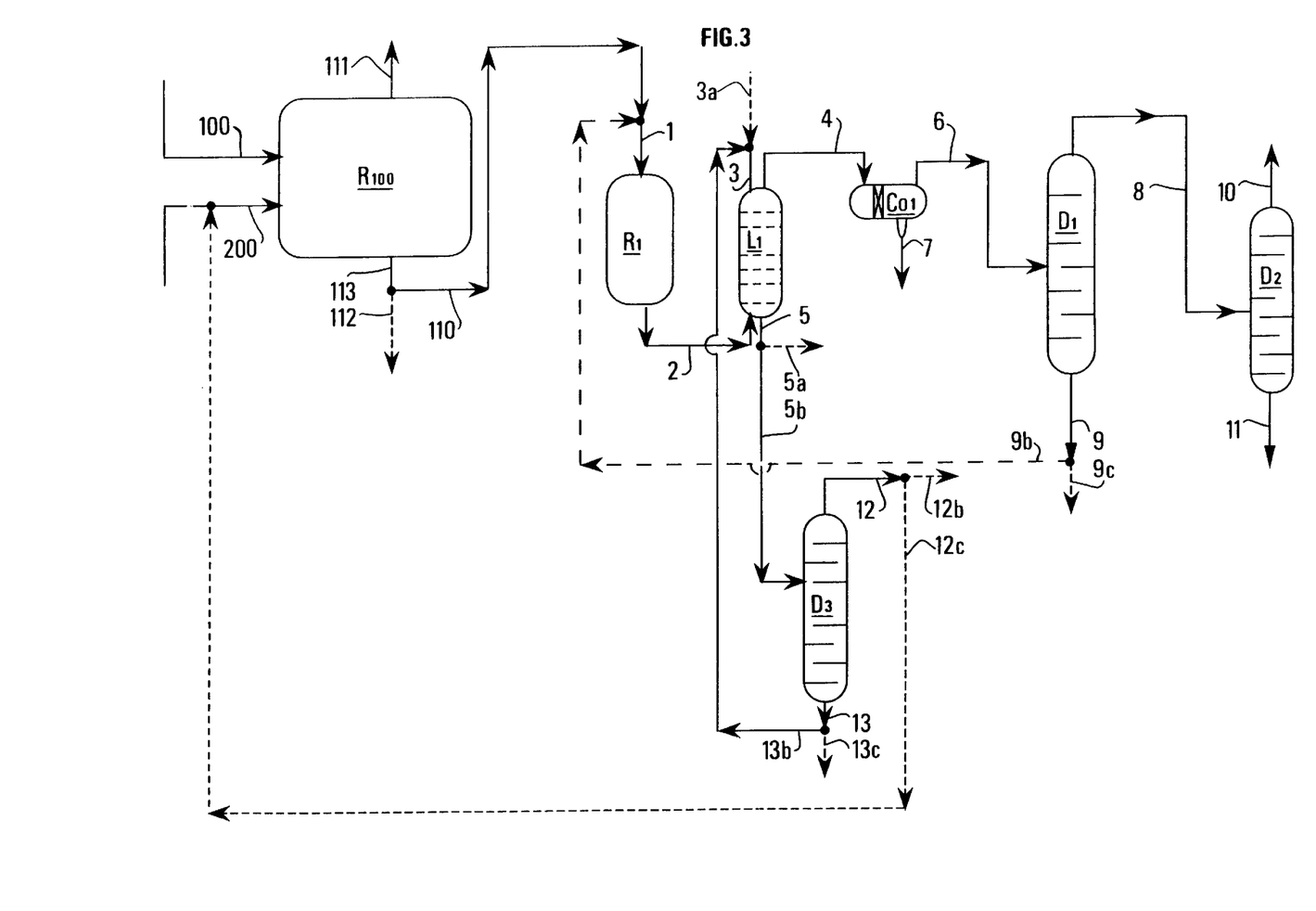

This implementation of the present invention is illustrated in FIG. 1. The hydrocarbon feed containing at least one tertiary olefin is introduced into an etherification and fractionation zone R100 via line 100. An alcohol makeup is also introduced into zone R100 via line 200 and, optionally, recycled alcohol, via lines 12c and 200. This zone contains an acid etherification catalyst. The product obtained by etherification of the hydrocarbon cut is split in this zone into an organic hydrocarbon fraction (O1) which leaves via line 111 and an organic fraction (E1) containing the ether which is formed which leaves via line 113. A portion of this organic fraction (E1) is sent via line 112 to the motor fuel pool and the other portion is sent to an ether decomposition zone R1 via line 110. A product (P1) containing at least one tertiary olefin, at least one alcohol, possibly ether which has not decomposed in this step c) and possibly light compounds is recovered via line 2 and sent to water washing extraction zone (L1) into which water for washing is introduced via line 3. An aqueous fraction (A1) containing water and the major portion of the alcohol initially present in product (P1) is obtained from this zone (L1) via line 5, and a fraction (B1) containing the major portion of the tertiary olefin initially present in product (P1) is obtained via line 4, fraction (B1) containing the tertiary olefin, water, possibly ether which has not decomposed in step c) and possibly light compounds and being substantially free of alcohol. This fraction (B1) is introduced via line 4 into a coalescer (Co1) from which an essentially aqueous fraction (La1) is recovered via line 7 and an organic fraction (Lb1) containing purified tertiary olefin (Ohp1) is recovered via line 6.

The process of the invention may comprise a number of variations which can in particular improve the quality of the recovered tertiary olefin and/or upgrading of the products. These variations are described below. These variations can be implemented separately or simultaneously, either in their totality or in combinations of two or more.

Within the context of the present invention, the aqueous fraction (A1) can be recovered as it is for sending to a water treatment section, as will be described below, or it can be split into an aqueous fraction which is depleted in alcohol which can, for example, be re-used as washing water or which can be sent to a water treatment section, and into an organic fraction which is enriched in alcohol which can, for example, be recovered and sent to an ether synthesis zone, preferably to the ether synthesis zone (R1) of step a).

One variation of the process of the present invention comprises a step f) (see FIGS. 1, 3, 4 and 5 in particular) in which at least a portion, or all, of fraction (A1) from step d) from line 5 is sent via lines 5b and 5d to a fractionation zone (D3). A portion of fraction (A1) can also be removed via lines 5 and 5a. From zone (D3), a fraction (G1) containing the major portion of the alcohol initially present in the portion of fraction (A1) is recovered via line 12 and an aqueous fraction (H1) which is practically free of the major portion of the alcohol initially present in the portion of fraction (A1) is recovered via line 13. In this implementation, at least a portion of fraction (G1) obtained from step f) containing alcohol can be sent, preferably via lines 12c and 200, to the ether synthesis zone (R100) of step a). It is also possible to send all of this alcohol to the ether synthesis zone. It is also possible to recover all or part of this alcohol via line 12b for other uses. It is also possible to recycle at least a portion, or all, of the aqueous fraction (H1) via lines 13, 13b and 3 to the water washing extraction zone (L1) of step d). When recycling is partial or non existent, part or all of the aqueous fraction (H1) from line 13 can, for example, be sent to a waste water treatment zone via line 13c.

In a further variation of the process of the present invention (see FIG. 1 in particular), at least part of the liquid fraction (La1) obtained from step e) is recycled via lines 7, 7b and 3 to the water extraction zone (L1) of step d). It is possible to recycle all of this fraction (La1) to water extraction zone (L1). When recycling is partial or not present, part or all of the aqueous fraction (La1) can, for example, be sent to a waste water treatment zone via lines 7 and 7c.

In a further variation of the process of the invention (see FIG. 1 in particular), at least a portion of the liquid fraction (La1) obtained from step e) is sent to the fractionation zone (D3) of step f) via lines 7, 7d and 5d.

In the above variations where water is recycled to zone (L1) either from the aqueous fraction (La1) from step e) or from aqueous fraction (H1) from step f), or from both of these fractions, the quantity of water used in extraction zone (L1) is adjusted if necessary using at least one means for introducing makeup water into zone (L1) via lines 3a and 3 (see FIGS. 1 to 5). This makeup of water can in particular compensate for loss of water by entrainment or due to saturation of the treated hydrocarbon stream, and can also replace any water which may have been purged.

In a further variation, the process of the present invention comprises a step g) (see, in particular, FIGS. 2 to 5) in which at least a portion of the liquid organic fraction (Lb1) (containing purified tertiary olefin (Ohp1)) from zone (Co1) of step e), preferably all of that fraction, is sent to a fractionation zone (D1) 5 via line 6 from which a fraction (E10) containing the major portion of the ether which has not decomposed in step c) is recovered via line 9 and an organic fraction (F1) containing the major portion of the tertiary olefin initially contained in fraction (Lb1) is recovered via line 8. Fraction (F1) contains purified tertiary olefin (Ohp2). In this implementation, at least a portion, preferably all, of fraction (E10) containing the major portion of the ether which has not decomposed in step c) is recycled to zone (R1) via lines 9, 9b and 1, line (9b) adding to line (110) from zone (R100) to form line 1. When recycling is partial or non existent, this portion of fraction (E10) can, for example, be sent to a gasoline pool or storage zone via lines 9 and 9c. In this implementation, accumulation of heavy compounds (dimers, MSBE) is largely avoided by dint of releasing a portion of fraction (E10) via line 9c.

In a further variation, when zone (D1) is present to carry out step g) (see FIG. 5 in particular), at least a portion, or all, of fraction (E10) containing the major portion of the ether which has not decomposed in step c) from zone (D1) of optional step g), is sent via lines 9, 9b and 9e to a purification zone (P) from which a heavy fraction is recovered via line 220 and sent, for example, to fuel pools and a lighter fraction containing purified ether is recovered via line 205 and sent via lines 210 and 1 (lines 210 and 110 forming line l) to ether decomposition zone (R1). In this variation, a further portion of fraction (E10) containing the major portion of the ether which has not decomposed in step c) can be sent directly to zone (R1) via lines 9, 9b, 200, 210 and 1.

In a further variation, when zone (D1) is present to carry out step g), the process of the present invention comprises a step h) (see FIG. 3 in particular) in which at least a portion of fraction (F1) from zone (D1), preferably all of that fraction, is sent to a fractionation zone (D2) via line 8 from which a fraction (Lg1) containing the majority of the light compounds initially present in that portion of fraction (F1) is recovered via line 10 and a fraction (Ohp3) containing the majority of the tertiary olefin initially contained in that portion of fraction (F1) is recovered via line 11. Fraction (Ohp3) essentially contains purified tertiary olefin.

In a still further variation, when zone (D1) is present to carry out step g) (see FIGS. 4 and 5 in particular), the process of the present invention comprises a step i) in which at least a portion of fraction (F1) from zone (D1), preferably all of that fraction, is sent via line 8 to a water washing extraction (L2) from which an aqueous fraction (A2) containing the major portion of the alcohol initially present in that portion of fraction (F1) is obtained via line 16, and a fraction (B2) containing the major portion of the tertiary olefin initially present in that portion of fraction (F1) is obtained via line 15, fraction (B2) containing the purified tertiary olefin (Ohp4), water, and possibly light compounds and being substantially free of alcohol.

In one embodiment of that variation (see FIG. 4 in particular), at least a portion of the aqueous fraction (A2) from step i), preferably all of that fraction, is sent via lines 16, 16b and 16d to fractionation zone (D3) of step f). In a further variation (see FIGS. 4 and 5 in particular), at least a portion of the aqueous fraction (A2) from step i), usually all of that fraction, is sent via lines 16, 16c and 3 to zone (L1). A portion of the aqueous fraction (A2) from step i) can also be recovered via lines 16, 16b and 16e for FIG. 4 or via lines 16 and 16e for FIG. for sending to a waste water treatment zone, for example.

In a further variation, when a zone (D1) carrying out step g) and a zone (L2) carrying out step i) are present (see FIG. 4 in particular), the process of the present invention comprises a step j) in which at least a portion of fraction (B2) from step i), preferably all of that fraction, is sent via line 15 to a fractionation zone (D2) from which a fraction (Lg2) containing the majority of the light compounds initially present in the portion of fraction (B2) introduced into step j) is recovered via line 10, and a fraction (Ohp5) containing the majority of the tertiary olefin initially contained in the portion of fraction (B2) introduced into step j) is recovered via line 11. Fraction (Ohp5) essentially contains purified tertiary olefin.

Figure 4:
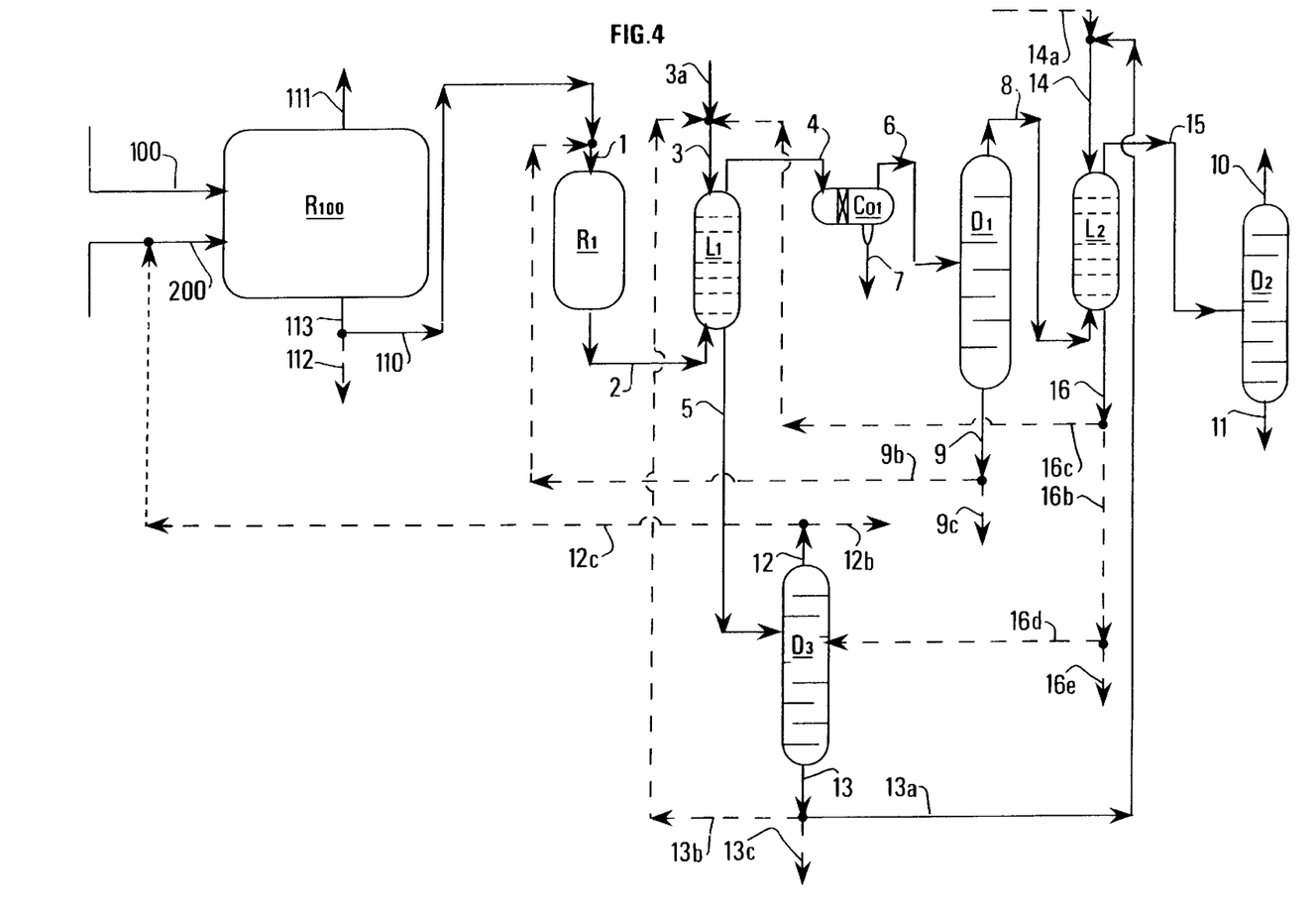
Figure 5:
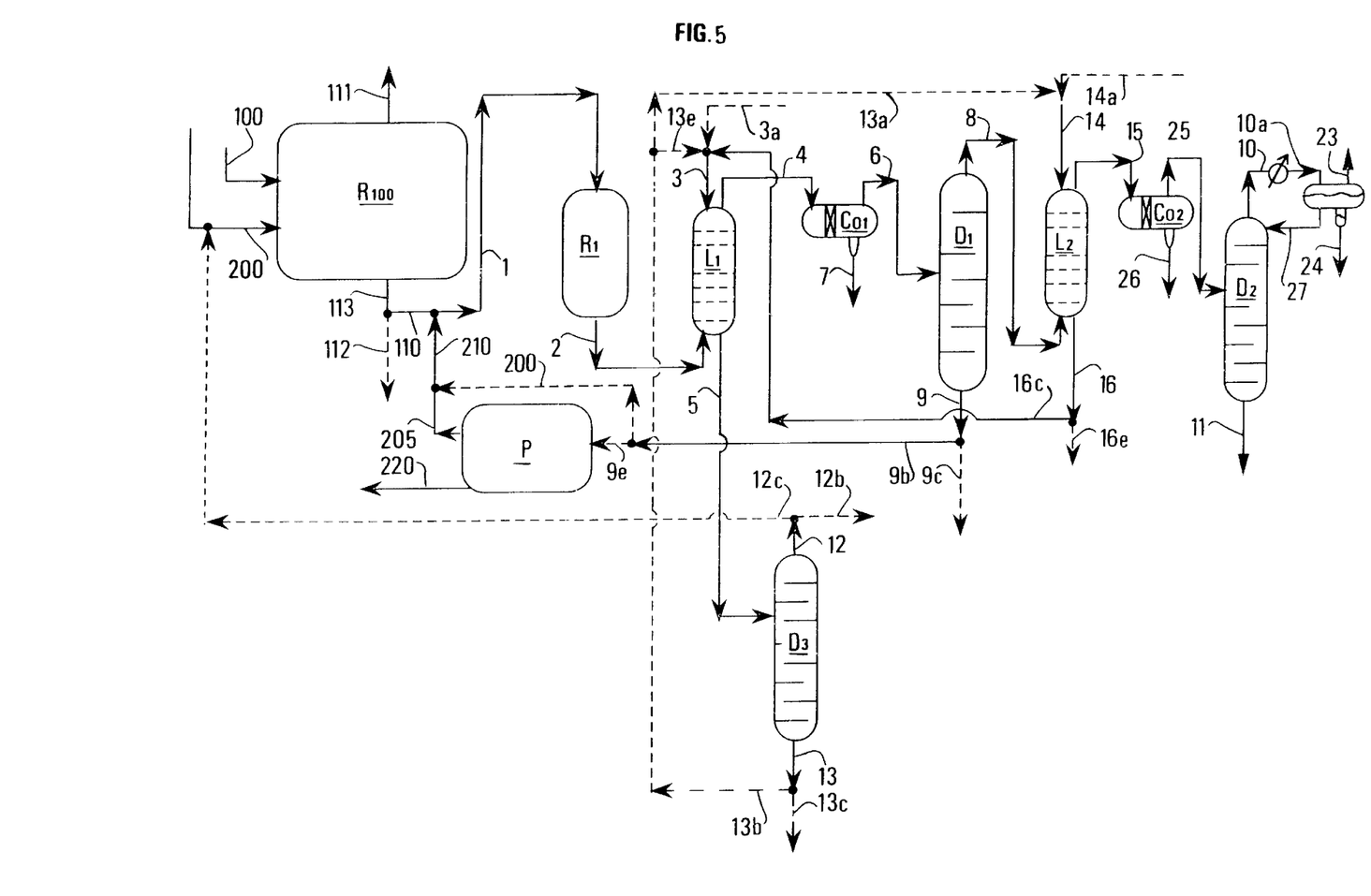

In a further variation, when a zone (D3) carrying out step g), a zone (D1) carrying out step h) and a zone (L2) carrying out step i) are present (see FIGS. 4 and 5 in particular), it is also possible to recycle at least a portion, or all, of the aqueous fraction (H1) from zone (D3) to extraction zone (L2) via lines 13, 13a and 14 (FIG. 4) (13, 13b, 13a and 14 in FIG. 5).

In a further variation, when a zone (D3) carrying out step g), a zone (D1) carrying out step h) and a zone (L2) carrying out step i) are present (see FIG. 5 in particular), in the process of the present invention, at least a portion of fraction (H1) from zone (D3) is recycled via lines 13, 13b, 13e and 3 to extraction zone (L1) and at least a further portion of fraction (H1) from step f) is recycled via lines 13, 13b, 13a and 14 to extraction zone (L2) and optionally, at least a further portion of fraction (H1) from step f) can, for example, be sent via lines 13 and 13c to a waste water treatment zone.

The quantity of water used in extraction zone (L2), when a zone (D3) carrying out step g), a zone (D1) carrying out step h) and a zone (L2) carrying out step i) are present, is adjusted if necessary using a means for introducing makeup water into zone (L2) via lines 14a and 14 (see FIGS. 4 and 5). This makeup of water can in particular compensate for loss of water by entrainment or due to saturation of the treated hydrocarbon stream, and can also replace water which may be purged.

In a further variation, when a zone (D1) carrying out step g) and a zone (L2) carrying out step i) are present (see FIG. 5 in particular), the process of the present invention comprises a step k) in which at least a portion of fraction (B2) from step i), preferably all of that fraction, is sent via line 15 to a separation zone (Co2) from which an aqueous liquid fraction (La2) is recovered via line 26 and an organic liquid fraction (Lb2) containing the major portion of the tertiary olefin initially present in that portion of fraction (B2) is recovered via line 25, fraction (Lb2) containing the purified tertiary olefin (Ohp6) and possibly light compounds.

In a further implementation of that variation (see FIG. 5 in particular), the process of the present invention also comprises a step l) in which at least a portion of fraction (Lb2) from step k), preferably all of that fraction, is sent via line 25 to a fractionation zone (D2) from which a fraction (Lg3) containing the major portion of the light compounds initially present in said portion of fraction (Lb2) is recovered via line 10 and a fraction (Ohp7) containing the major portion of the tertiary olefin initially contained in said portion of fraction (Lb2) is recovered via line 11. Fraction (Ohp7) is essentially very pure tertiary olefin.

In a particular implementation (see FIG. 5 in particular) of the present invention, zone (D2) in the various variations described above comprises at least one means for recovering a substantially anhydrous light fraction from fraction [Lg1—step h), Lg2—step j) or Lg3—step l)] in a step m). This means usually comprises a condenser into which at least part of the gaseous light fraction (Lg1, Lg2 or Lg3) is introduced via line 10 and leaves at least partially liquefied via line 10a; this splits at least part of the fraction (Lg1, Lg2 or Lg3) into a substantially anhydrous light fraction (Lg4) and an aqueous fraction (Le) which is recovered via line 24. This means is, for example, a separator drum provided with at least one means, for example a boot, for decanting and extracting an aqueous fraction. In this case, the substantially anhydrous light fraction is normally split into a gaseous fraction which is evacuated via line 23, for example flared off. and a liquid fraction at least a portion of which is returned to fractionation zone (D2) via line 27.

In a further embodiment of this particular implementation, at least part of the fraction (Lg1, Lg2 or Lg3) (or substantially anhydrous light fraction (Lg4) obtained from fraction (Lg1, Lg2 or Lg3)) is sent to a catalytic cracking zone. In a further variation, at least part of the fraction (Lg1 or Lg2 or Lg3 or Lg4) is sent to an ether synthesis zone, preferably the ether synthesis zone of step a).

All or part of the various aqueous fractions [(La1)—step e); (H1)—step f); (A2)—step i); (La2)—step k); (Le)—step m)] which may be obtained in the various implementations of the present invention can be recycled to washing zone (L1) if only one washing zone exists or to one or other of washing zones (L1) and (L2) when there are two washing zones, or partly to one and partly to the other.

The conditions under which step a) of the present invention are carried out are conventional conditions which are well known to the skilled person for synthesising a tertiary alkyl ether from a hydrocarbon cut containing at least one tertiary olefin which is etherifiable by at least one alcohol, in particular an alcohol containing 1 to 6 carbon atoms per molecule, usually methanol or ethanol. The hydrocarbon cuts used in the context of the present invention contain at least one tertiary olefin and generally other saturated or unsaturated hydrocarbons such as other olefins, paraffins, possibly a small proportion of water, and/or oxides of carbon. The purified tertiary olefins which can be prepared using the present invention are compounds in which one carbon atom of the olefinic bond is branched. These compounds generally contain 4 to 10 carbon atoms per molecule, preferably 4 to 8 carbon atoms per molecule and usually 4 to 6 carbon atoms per molecule. Examples which can be cited are isobutene, 2-methyl-1-butene, 2-methyl-2-butene, tertiary hexenes, tertiary octenes and tertiary decenes. Examples which can be cited are $C_4$ and/or $C_5$ cuts from refining or from petrochemistry, such as $C_4$ and/or $C_5$ cuts from steam cracking, normally after diene extraction, $C_4$ and/or $C_5$ catalytic cracking cuts, cuts from isomerisation (hydroisomerisation or skeletal isomerisation) and cuts obtained by paraffin dehydrogenation. Ether synthesis is usually carried out in the presence of an acid catalyst, usually a solid acid catalyst selected from the group formed by organic acidic resins (for example sulphonic resins) and mineral acid resins which are generally solid under the ether synthesis reaction conditions (for example grafted mineral solids comprising at least one organic sulphonic group for example an alkylsulphonic, arylsulphonic, or alkylarylsulphonic group, in particular grafted polysiloxanes and more particularly those grafted with at least one alkylsulphonic group). The catalyst can be a commercial resin such as Amberlyst 15 or 35 resin from ROHM & HAAS or M 31 resin from DOW-CHEMICAL, or a commercially available grafted polysiloxane. In step a), the quantity of alcohol used in normally such that the alcohol/tertiary olefin molar ratio present in the feed is about 0.5:1 to about 8:1, usually 0.8:1 to about 5:1, more usually about 0.9:1 to about 4:1. The reaction temperature is normally about 20° C. to about 120° C., usually about 30° C. to about 100° C., more usually about 40° C. to about 90° C. The HSV (hourly space velocity), the volume of feed per volume of catalyst per hour, is normally about 0.005 to about 100, usually about 0.01 to about 50 and more usually about 0.1 to about 10. The pressure is normally selected so that the constituents present in the reaction zone are in the liquid state. The absolute pressure in this etherification zone is about 1 bar to about 40 bar, normally about 1 bar to about 25 bar (1 bar equals 0.1 MPa).

The conditions for implementing step b) tor separating the product from step a) into an organic fraction (O1) containing practically no tertiary alkyl ether and an organic fraction (E1), preferably containing practically all of the tertiary alkyl ether formed during step a), are conventional conditions which depend on the compounds present in the product from step a). This separation can be carried out under conditions of varying severity to obtain a fraction (O1) still containing a small proportion of ether. The skilled person will be able to select the operating conditions to obtain the desired separation. The conditions are usually selected so as to obtain a fraction (E1) containing almost all of the ether formed during step a). Within the context of the invention, the etherification zone of step a) can be distinct from the separation or fractionation zone of step b), or an apparatus can be used which comprises a mixed reaction and fractionation zone (generally a catalytic distillation column) such as that described in a number of prior art patents and other publications. In the case of a process in which MTBE is produced in step a), the separation zone which is generally a distillation separation column normally operates at an absolute pressure of about 1 to about 30 bar, identical to or different from that prevailing in the etherification zone. This column normally comprises 3 to 80 theoretical plates, usually 10 to 50 theoretical plates.

The conditions under which step c) of the present invention are carried out are conventional tertiary alkyl ether decomposition conditions which are well known to the skilled person. In a preferred implementation, this step c) is carried out without adding supplementary water to the product introduced into the decomposition zone. However, it is possible to add a certain quantity of water, for example up to the limit of the solubility of water in the ether which is to be decomposed. Normally, the conditions under which step c) is carried out in zone (R1) are selected so that the major portion of the tertiary alkyl ether decomposes to produce an alcohol and a tertiary olefin. In this zone (R1), the absolute pressure is normally about 1 to about 30 bars, preferably about 1 to about 12 bars, the temperature is normally in the range 50° C. to 300° C., preferably in the range 100° C. to 250° C., and the HSV (hourly space velocity) is normally in the range 0.1 to 200 $h^{-1}$, usually in the range 0.5 to 100 $h^{-1}$. In this zone (R1), any of the acid catalysts known to the skilled person can be used. Solid acid catalysts are preferably used. Thus the catalyst can be selected from the group formed by organic acid resins and mineral acid resins which are generally solids under the ether decomposition reaction conditions. Of these compounds, those selected from the group formed by grafted mineral solids containing at least one alkylsulphonic, arylsulphonic or alkylarylsulphonic type organic group are usually used. In one preferred implementation of this step c), a catalyst selected from the group formed by polysiloxanes grafted with at least one alkylsulphonic group is used.

In step d), at least a portion of product (P1) from step c) is sent to a water washing extraction zone (L1), in which the quantity of water used for washing is normally such that the ratio between the volume of that quantity of water introduced into the extraction zone and that of the portion of product (P) introduced into the extraction zone ($V_{water}/V_P$) is about 0.005 to about 20 by volume. This quantity of water is usually such that the ratio $V_{water}/V_P$ is about 0.005 to about 10, preferably about 0.01 to about 5, more preferably about 0.02 to about 1. The water flow rate in this washing zone (L1) is usually regulated so as to maintain a foundation level in the water and alcohol fractionation zone (D3) when such a zone (D3) is present. This foundation level can be defined as the minimum level required for the zone to operate properly. This parameter is a conventional parameter which is well known to the skilled person. The regulation is often carried out manually by the operators, but it is possible for this regulation to be carried out by an automatic Level Control Regulation circuit. Regardless of the selected mode of regulation, the quantity of water can generally be adjusted using a means for introducing makeup water into zone (L1). This makeup water can in particular compensate for loss of water due to entrainment and/or saturation of the treated hydrocarbon stream and can replace any purged water. This extraction zone (L1) is normally a tray column which operates at a temperature of about 1° C. to about 100° C., preferably about 10° C. to about 60° C. The absolute pressure in this zone is about 1 to about 20 bars, normally about 1 to about 15 bars, identical to or different from that prevailing in the decomposition zone.

Step e), which comprises a zone for separating at least a portion of the fraction from step d) into an aqueous liquid fraction (La1) and an organic liquid fraction (Lb1) in a zone (L1), is a conventional step. This step is normally carried out in an apparatus termed a coalescer, in which water collects in the lower part of the apparatus by coalescence. The temperature and pressure conditions in this zone are in the same ranges as those prevailing in water extraction zone (L1). The pressure (or respectively the temperature) can be identical to or different from that in zone (L1) of step d). In zone (Co1), the free water contained in the product from step d) is separated out. Further, this zone (Co1) also usually acts as a feed drum for the tertiary olefin purification zone (D1) when such a zone (D1) is present. Any other means known to the skilled person can be used in the present invention. As an example, an absorbent with preferential selectivity for the aqueous or organic fraction could be used.

The general conditions for carrying out optional step g) for fractionation of at least a portion of fraction (Lb1) from step e) are generally selected as a function of the characteristics of the residual ether and the tertiary olefin formed, to obtain the desired separation between a fraction containing the residual ether as its major portion and a fraction containing the olefin as its major portion. Thus, for example, in the case of MTBE decomposition and isobutene formation, the absolute pressure in the fractionation zone is about 1 to about 15 bars, usually about 1 to about 10 bars, identical to or different from that prevailing in zone (Co1). The column bottom temperature depends on the pressure prevailing in that column and the composition of the bottoms product. For a unit treating 1 kg/h of MTBE, the distillation column (D1) normally comprises 3 to 80 theoretical plates, usually 5 to 50 theoretical plates.

Optional step h) for fractionating at least a portion of fraction (F1) from zone (D1) carrying out step g) when such a zone (D1) is present, in a fractionation zone (D2), can recover a fraction containing the major portion of the tertiary olefin initially present in that portion of fraction (F1) and a fraction (Lg1) containing the major portion of the light compounds initially present in that portion of fraction (F1). The general operating conditions of step h) in the case of MTBE decomposition and isobutene formation are generally such that the absolute pressure in the fractionation zone, which is generally a distillation column, is about 1 to about 15 bars, usually about 1 to about 10 bars, identical to or different from that prevailing in zone (D1) of step g). The column bottom temperature depends both on the pressure prevailing in that column and the desired purity of the tertiary olefin recovered from the column bottom. For a unit treating 1 kg/h of MTBE, the distillation zone (D2) normally comprises 2 to 80 theoretical plates, usually 3 to 60 theoretical plates.

Optional step f) for fractionating, in a zone (D3), at least a portion of aqueous fraction (A1), containing the major portion of the alcohol initially present in product (P1) from step c), separates the portion of fraction (A1) into a fraction (G1) containing the major portion of the alcohol initially present in fraction (A1) and an aqueous fraction (H1) which is free of the major portion of the alcohol initially present in that portion. It is normally carried out in a distillation column (D3) at an absolute pressure of about 1 to about 12 bars, preferably about 1 to about 8 bars, identical to or different from that prevailing in water extraction zone (L1) of step d). The column bottom temperature depends on the pressure prevailing in that column and is normally about 50° C. to about 300° C., usually about 65° C. to about 200° C. The column normally comprises 2 to 80 theoretical plates, usually 3 to 60 theoretical plates.

In optional step i), at least a portion of fraction (F1) from zone (D1) of step g) when such a zone (D1) is present, this fraction is sent to a water washing extraction zone (L2) in which the quantity of water used for washing is normally such that the ratio between the volume of that quantity of water introduced into the extraction zone and that of the portion of fraction (F1) introduced into the extraction zone ($V_{water}/V_{F1}$) is about 0.005 to about 20 by volume. This quantity of water is usually such that the ratio $V_{water}/V_{F1}$ is about 0.005 to about 10, preferably about 0.01 to about 5, more preferably about 0.02 to about 1. The water flow rate in this washing zone (L2) can also be more precisely regulated so as to maintain a foundation level in the water and alcohol fractionation zone (D3) when such a zone (D3) is present. This foundation level can be defined as the minimum level required for zone (D3) to operate properly. This parameter is a conventional parameter which is well known to the skilled person. The regulation is often carried out manually by the operators, but it is possible for this regulation to be carried out by an automatic Level Control Regulation circuit. Regardless of the selected mode of regulation, the quantity of water can generally be adjusted using a means for introducing makeup water into water washing column (L2) of step i) and/or zone (L1) of step d). This makeup water can in particular compensate for loss of water due to saturation of the treated hydrocarbon stream and can replace any purged water. This extraction zone (L2) is normally a tray column which operates at a temperature of about 1° C. to about 100° C., preferably about 10° C. to about 60° C. The absolute pressure in this zone is about 1 to about 20 bars, normally about 1 to about 15 bars, identical to or different from that prevailing in the fractionation zone of step g).

In optional step j), when a zone (D1) carrying out step g) and a zone (L2) carrying out step i) are present at least a portion of the fraction (B2) containing the major portion of the tertiary olefin obtained from step i) is sent to a fractionation zone (D2) from which a fraction containing the major portion of the tertiary olefin (Ohp5) initially present in the portion of fraction (B2) is recovered and a fraction (Lg2) containing the major portion of the light compounds initially present in that portion of fraction (B2) is recovered. The general operating conditions for this step j) for MTBE decomposition and isobutene formation are generally such that the absolute pressure in zone (D2) which is a distillation column is about 1 to about 15 bar, usually about 1 to about 10 bar, identical to or different from that prevailing in washing zone (L2) of step i). The column bottom temperature depends both on the pressure prevailing in the column and the desired purity of the tertiary olefin recovered from the column bottom. For a unit treating 1 kg/h of MTBE, the distillation column (D2) normally comprises 2 to 80 theoretical plates, usually 3 to 60 theoretical plates.

Optional step k), when a zone (D1) carrying out step g) and a zone (L2) carrying out step i) are present, comprises a zone for separating at least a portion of product (B2) from step i) into an aqueous liquid fraction (La2) and an organic liquid fraction (Lb2). It is normally carried out in a zone (Co2) in an apparatus termed a coalescer, in which water collects in the lower portion of the apparatus by coalescence. The temperature and pressure conditions in this zone are in the same ranges as those in water extraction step i). The pressure (or, respectively, the temperature) can be identical to or different from that in step i). In this zone, free water contained in product (B2) from step i) is separated out. Further, the zone also acts as a feed zone or drum for a tertiary olefin purification zone (D2), when such a zone (D2) is present. Any other known means can be used within the context of the present invention. As an example, the use of an absorbent with preferential selectivity for the aqueous or the organic fraction can be used. Fraction (Lb2) contains the purified tertiary olefin (Ohp6) and possibly light compounds.

The general conditions for carrying out optional step l) for fractionating, in a zone (D2), at least a portion of fraction (Lb2) from preceding step k) into an aqueous liquid fraction (La2) and a liquid organic fraction (Lb2) are selected as a function of the characteristics of the tertiary olefin formed, to obtain the desired separation between a fraction containing the major portion of the light compounds and a fraction containing the major portion of the olefin. Thus, in the case of MTBE decomposition and isobutene formation, for example, the absolute pressure in the fractionation zone, which is generally a distillation column, is about 1 to about 15 bars, usually about 1 to about 10 bars, identical to or different from that prevailing in zone (Co2) of step k). The column bottom temperature depends on the pressure prevailing in that column and the composition of the bottoms product. For a unit treating 1 kg/h of MTBE, the distillation column (D2) normally comprises 3 to 80 theoretical plates, usually 5 to 50 theoretical plates.

The following example illustrates the invention without limiting its scope.

EXAMPLE

A pilot type unit was used which comprised two tube reactors (R100) and (R1), with 20 milliliter and 10 milliliter volumes respectively. The first reactor (R100) contained 6 grams of Amberlyst 15 resin sold by ROHM & HAAS and operated at a relative pressure of 10 bar, at an average temperature of 50° C. It was supplied with a $C_4$ cut from catalytic cracking containing 20% by weight of isobutene and by pure methanol sold by ALDRICH as a product with a purity of over 99% by weight. The quantity of methanol was adjusted so that the methanol/isobutene molar ratio introduced into reactor (R100) was 1.2. The reactor operated at an HSV of 0.5 $h^{-1}$. Under the selected conditions, conversion of isobutene to MTBE was 97%.

The second reactor (R1) contained 3 grams of commercially available catalyst based on polysiloxanes grafted with at least one alkylsulphonic group. Reactor (R1) was supplied with a feed containing 100% by weight of MTBE, at an HSV of 15 $h^{-1}$, the relative pressure in the reactor was 7 bar and the average temperature was 160° C. Table 1 shows the composition of the feed introduced into MTBE decomposition reactor (R1) and the composition of the product recovered from the outlet from reactor (R1).

TABLE 1

|  | Feed (wt %) | R1 effluent (wt %) |
|---|---|---|
| MTBE | 100 | 10 |
| Isobutene |  | 56.1 |
| Methanol |  | 32.1 |
| DME |  | 0.5 |
| Dimers |  | 1.1 |
| $H_2O$ |  | 0.2 |

The various purification sections were calculated using software produced by American company SIMSCI (SIMulation SCIence INC.) under the trade name Pro II.

A distillation column (Co1), operating at a relative pressure of 7 bar, comprising 10 theoretical plates, was used in step b) of the process of the invention to obtain a bottoms product (E1) and an overhead product (O1). (This simulated fractionation of the product from step a) for etherification of the isobutene contained in the $C_4$ cut).

A water washing extraction column (L1), a tray column operating at a temperature of 30° C. and a relative pressure of 12 bars, was used in step d) of the process of the invention to obtain an aqueous fraction (A1) and an organic fraction (B1). (This simulated extraction of methanol from the effluent from MTBE decomposition step c)).

A coalescer type (Co1) system for extracting free water entrained in step d) in fraction (B1), enabled an aqueous fraction (La1) and an organic fraction (Lb1) to be obtained. It operated at a relative pressure of 12 bar and a temperature of 30° C.

A distillation column (D1), operating at a relative pressure of 7 bar, comprising 20 theoretical plates used in step g) of the process of the invention was used to obtain a bottoms product (E10) and an overhead product (F1).

A distillation column (D2), the last step in the isobutene purification, operating at a relative pressure of 7 bars and comprising 20 theoretical plates, was used in step h) of the process of the invention to obtain a bottoms product (Ohp3) which was purified isobutene and an overhead product (Lg1) containing light compounds.

Column (Co1) was supplied with the product from the etherification reactor. Product (E1) recovered from the bottom of column (Co1) was used to supply reactor (R1). Extraction column (L1) was supplied with MTBE decomposition product (P1) (effluent from reactor R1) where it was washed with a quantity of water the flow rate of which was half that of (P1). An aqueous fraction (A1) containing the major portion of the methanol contained in (P1) and a hydrocarbon fraction (B1) containing a small quantity of entrained free water was recovered. This fraction of free water was finally eliminated after decanting in the decanting system (Co1) in the form of a fraction (La1) and an organic hydrocarbon fraction (Lb1) was recovered. This hydrocarbon fraction (Lb1) was treated in column (D1) to produce a fraction (E10) containing principally ether which had not decomposed in reactor (R1) from the bottom of the column and a fraction (F1) containing principally isobutene was recovered overhead. Fraction (F1) was sent to column (D2) from which a light fraction (Lg1) containing dimethyl ether (DME) in particular was recovered overhead and a fraction (Ohp3), high purity isobutene, was recovered from the bottom.

The material balances are given in Tables 2, 3 and 4 below. Table 2 shows the material balance for MTBE synthesis. Tables 3 and 4 show the material balance for MTBE decomposition and the production of high purity isobutene.

TABLE 2

|  | Feed R100 (weight) | Effluent R100 (weight) | Col head (weight) | Col bottom (weight) |
|---|---|---|---|---|
| Isobutene | 20 | 0.6 | 0.6 |  |
| C4 ex isobutene | 80 | 80 | 80 |  |
| Methanol | 13.7 | 2.7 | 2.7 |  |
| MTBE | 0 | 30.4 | 0 | 30.4 |
| Total | 113.7 | 113.7 | 83.3 | 30.4 |

TABLE 3

|  | Effluent R1 | Washing water column L1 | Fraction A1 column L1 | Fraction B1 column L1 | Aqueous fraction La1 extracted by Col | Organic fraction extracred by Col |
|---|---|---|---|---|---|---|
| MTBE | 10 |  |  | 10 |  | 10 |
| Iso-butene | 56.1 |  |  | 56.1 |  | 56.1 |
| Meth-anol | 32.1 |  | 32 | 0.1 |  | 0.1 |
| DME | 0.5 |  |  | 0.5 |  | 0.5 |
| Dimers | 1.1 |  |  | 1.1 |  | 1.1 |
| $H_2O$ | 0.2 | 50 | 48 | 2.2 | 2.18 | 0.02 |
| Flow rate (g/h) | 100 | 50 | 80 | 70 | 2.18 | 67.82 |

TABLE 4

|  | Fraction F1 column D1 | Fraction E10 column D1 | Fraction Lg1 column D2 | Fraction Ohp3 column D2 |
|---|---|---|---|---|
| MTBE |  | 10 |  |  |
| Isobutene | 56.1 |  | 1.6 | 54.5 |
| Methanol |  |  | 0.1 |  |
| DME | 0.5 |  | 0.45 | 0.05 |
| Dimers |  | 1.1 |  |  |
| $H_2O$ | 0.02 |  | 0.02 |  |
| Flow rate (g/h) | 56.72 | 11.1 | 2.17 | 54.55 |
| Isobutene purity (%) |  |  |  | 99.9% |

This example shows that carrying out the process of the invention can produce, from a $C_4$ cut containing isobutene, an isobutene in a purity of 99.9% with an overall conversion of 83% without optimisation, i.e., with no recycling The conversion can be improved by using a variety of recycling stages, including that of the bottoms product from column (D1) [fraction E10 obtained from step g)] to MTBE decomposition step c); a high purity isobutene yield of over 95% can then be obtained.

We claim:

1. A process for the production of a tertiary olefin and/or a tertiary alkyl ether from a hydrocarbon cut containing at least one etherifiable tertiary olefin, the process comprising:
    a) a step for forming at least one tertiary alkyl ether by bringing at least one hydrocarbon cut containing at least one etherifiable tertiary olefin into contact with at least one alcohol, in a reaction zone containing an etherification catalyst, under conditions for transforming at least a portion of the tertiary olefin into a tertiary alkyl ether;
    b) a fractionation step for separating the major portion of the product from step a) into an organic fraction (O1) which is depleted in tertiary alkyl ether and an organic fraction (E1), enriched in the tertiary alkyl ether;
    c) a step for decomposing at least a portion of the tertiary alkyl ether contained in the organic fraction (E1) from step b), in a reaction zone (R1) containing a catalyst for decomposing said ether, into a product (P1) containing at least one alcohol and at least one tertiary olefin;
    d) a step for purifying at least a portion of product (P1) from step c) in a water washing extraction zone (L1) from which an aqueous fraction (A1) containing the major portion of the alcohol initially present in said portion of product (P1) and a fraction (B1) containing the major portion of the tertiary olefin initially present in product (P1) are obtained, said fraction (B1) containing said tertiary olefin, water, possibly ether and possibly light compounds;

said process being characterized in that it comprises a step e) in which at least a portion of fraction (B1) is sent to a separation zone (Co1), from which a liquid aqueous fraction (La1) and a liquid organic fraction (Lb1) containing the major portion of the tertiary olefin initially present in said portion of the fraction (B1) are recovered, said fraction (Lb1) containing said tertiary olefin and possibly ether, possibly light compounds and possibly heavy compounds.

2. A process according to claim 1, further comprising recycling at least a portion of the liquid aqueous fraction (La1) obtained from step e) to water extraction zone (L1) of step d).

3. A process according to claim 1, further comprising a step f) in which at least a portion of fraction (A1) from step d) is sent to a fractionation zone (D3) from which a fraction (G1) containing the major portion of the alcohol initially present in said portion of fraction (A1) and an aqueous fraction (H1) which is practically free of the major portion of the alcohol initially present in said portion of fraction (A1) are recovered.

4. A process according to claim 3, further comprising passing at least a portion of fraction (G1) to a zone for synthesising ether (R100) of step a).

5. A process according to claim 3, further comprising recycling at least a portion of the aqueous fraction (H1) to the water extraction zone (L1) of step d).

6. A process according to claim 1, further comprising introducing makeup water into the water washing extraction zone (L1) of step d).

7. A process according to claim 1, further comprising passing at least a portion of the liquid organic fraction (Lb1) from zone (Co1) of step e) to a fractionation zone (D1) from which a fraction (E10) containing the major portion of the ether not decomposed in step c) and a fraction (F1) containing the major portion of the tertiary olefin initially contained in said fraction (Lb1) are recovered.

8. A process according to claim 7, further comprising recycling at least a portion of the fraction (E10) to zone (R1) of tertiary alkyl ether decomposition step c).

9. A process according to claim 7, further comprising a step h) in which at least a portion of fraction (F1) is sent to a fractionation zone (D2) from which a fraction (Lg1) containing the majority of the light compounds initially present in said portion of fraction (F1) and a fraction (Ohp3) containing the majority of the tertiary olefin initially present in said portion of fraction (F1) are recovered.

10. A process according to claim 7, further comprising a step i) in which at least a portion of fraction (F1) is sent to a water washing extraction zone (L2) from which an aqueous fraction (A2) containing the major portion of the alcohol initially present in said portion of fraction (F1) and a fraction (B2) containing the major portion of the olefin initially present in said portion of fraction (F1) are obtained.

11. A process according to claim 10, further comprising a step j) in which at least a portion of fraction (B2) from step i) is sent to a fractionation zone (D2) from which a fraction (Ohp5) containing the major portion of the olefin initially present in said portion of fraction (B2) and a fraction (Lg2) containing the majority of the light compounds initially present in said portion of fraction (B2) are obtained.

12. A process according to claim 10, further comprising a step k) in which at least a portion of fraction (B2) from step i) is sent to a separation zone (Co2) from which an aqueous liquid fraction (La2) and an organic liquid fraction (Lb2) containing the major portion of the tertiary olefin initially present in said portion of fraction (B2) are recovered, said portion of fraction (B2) containing said tertiary olefin, possibly ether and possibly light compounds.

13. A process according to claim 12, further comprising a step l) in which at least a portion of fraction (Lb2) from step k) is sent to a fractionation zone (D2) from which a fraction (Ohp7) containing the major portion of the olefin initially present in said portion of fraction (Lb2) and a fraction (Lg3) containing the majority of the light compounds initially present in said portion of fraction (Lb2) are recovered.

14. A process according to claim 10 wherein, when a zone (D3) carrying out step f) is present, at least a portion of the aqueous fraction (A2) from step i) is sent to the fractionation zone (D3) of step t).

15. A process according to claim 10, further comprising passing at least a portion of the aqueous fraction (A2) from step i) to the water washing extraction zone (L1) of step d).

16. A process according to claim 10, further comprising reclining at least a portion of the aqueous fraction (H1) from step f) to the water extraction zone (L2) of step i).

17. A process according to claim 10, comprising introducing makeup water into the water washing extraction zone (L2) of step i).

18. A process according to claim 9, wherein the fractionation zone (D2) from which a fraction containing the majority of light compounds (Lg1 or Lg2 or Lg3) is recovered comprises further fractionated to obtain a substantially anhydrous light fraction (Lg4).

19. A process according to claim 18, wherein said fraction (Lg4) is obtained by condensing at least a portion of the fraction (Lg1 or Lg2 or Lg3).

20. A process according to claim 18, further comprising recovering an aqueous fraction and recycling of an organic liquid fraction to said fractionation zone (D2).

21. A process according to claim 18, further comprising recovering at least a portion of said fraction (Lg1 or Lg2 or Lg3 or Lg4) to a catalytic cracking zone.

22. A process according to claim 18, further comprising sending at least a portion of said fraction (Lg1 or Lg2 or Lg3 or Lg4) to the ether synthesis zone (R100).

23. A process according to claim 7, further comprising sending at least a portion of fraction (E10) from step g), containing the major portion of ether which has not decomposed in step c), to a purification zone (P) from which a heavy fraction is recovered and a lighter fraction containing purified ether is recovered which is sent to the ether decomposition zone R1 of step c).

* * * * *